United States Patent [19]
Connell

[11] Patent Number: 6,098,617
[45] Date of Patent: *Aug. 8, 2000

[54] DEVICE FOR ADMINISTERING/SAMPLING INHALANT/EXPIRED GASES IN AN ORO/NASOPHARYNGEAL AIRWAY

[76] Inventor: Donald G. Connell, 937 Bridle Path Rd., Allentown, Pa. 18103

[ * ] Notice: This patent is subject to a terminal disclaimer.

[21] Appl. No.: 09/076,210

[22] Filed: May 12, 1998

Related U.S. Application Data

[63] Continuation-in-part of application No. 08/985,829, Dec. 5, 1997, Pat. No. 5,937,858.

[51] Int. Cl.⁷ .................................................. A61M 16/00
[52] U.S. Cl. ........................... 128/200.26; 128/207.14; 128/207.18; 128/201.25; 128/911
[58] Field of Search ............... 128/200.26, 207.14, 128/207.15, 207.18, 203.12, 911, 205.19, 201.25; 600/531, 532

[56] References Cited

U.S. PATENT DOCUMENTS

| | | | |
|---|---|---|---|
| 4,197,858 | 4/1980 | Osborn | 600/531 |
| 4,821,715 | 4/1989 | Downing | 128/207.18 |
| 5,050,615 | 9/1991 | Malkamäki | 600/532 |
| 5,339,808 | 8/1994 | Don Michael | 128/207.15 |
| 5,400,778 | 3/1995 | Jonson et al. | 128/205.19 |
| 5,497,768 | 3/1996 | Lomholt | 128/207.15 |
| 5,606,968 | 3/1997 | Mang | 128/207.15 |
| 5,765,559 | 6/1998 | Kim | 128/207.15 |
| 5,906,204 | 5/1999 | Beran et al. | 128/207.14 |
| 5,937,858 | 8/1999 | Connell | 128/207.14 |

*Primary Examiner*—John G. Weiss
*Assistant Examiner*—V. Srivastava
*Attorney, Agent, or Firm*—Warren W. Kurz

[57] ABSTRACT

A device adapted for use with a conventional oral or nasopharyngeal airway for delivering an inhalant gas to a proximal end of said airway, and for sampling exhalant gas at a distal end of said airway, comprises a pair of conduits which are adapted to slide into an internal passage of the airway to provide an inhalant gas at the proximal end therof and/or to sample expired gas at the distal end thereof when the airway is being used.

7 Claims, 4 Drawing Sheets

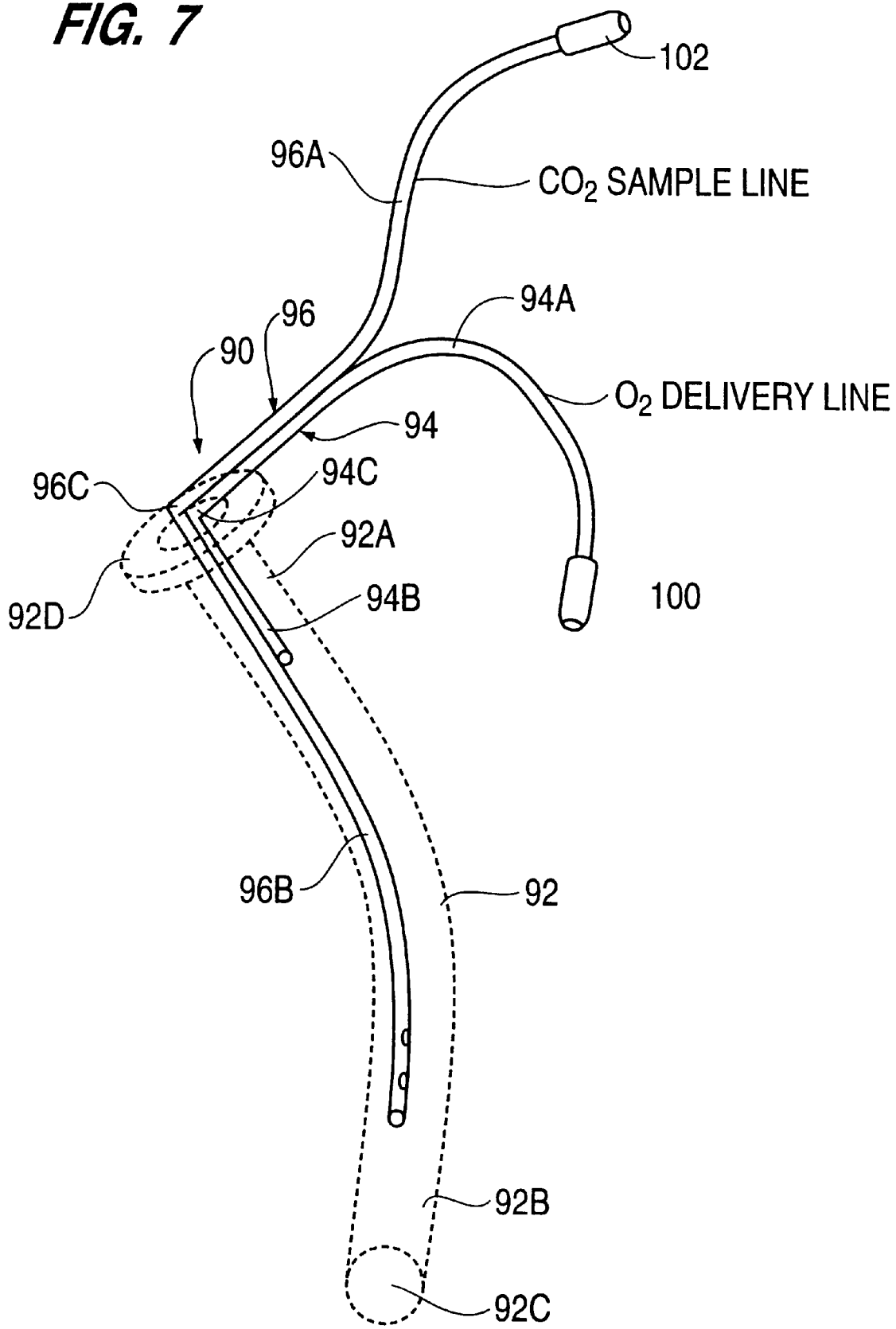

DEVICE FOR ADMINISTERING/SAMPLING INHALANT/EXPIRED GASES IN AN ORO/NASOPHARYNGEAL AIRWAY

CROSS REFERENCE TO RELATED APPLICATION

Reference is made to the commonly owned U.S. patent application Ser. No. 08/985,829, filed on Dec. 5, 1997 in the name of Donald G. Connell and entitled "ORO/NASOPHARENGEAL AIRWAY FOR ADMINISTERING/SAMPLING INHALANT/EXHALANT GASES", now U.S. Pat. No. 5,937,858, of which this application is a continuation-in-part.

BACKGROUND OF THE INVENTION

1. Field of the Invention

The present invention relates to improvements in pharyngeal airways of the type used during surgical and other medical procedures to prevent obstruction of the pharynal region of the alimentary canal, for example, while a patient is under anesthesia. More particularly, the invention relates to a pharyngeal airway which, in addition to being adapted to maintain a patient's airway open during a medical procedure, is also adapted to administer an inhalant gas (e.g., oxygen) and/or sample an exhalant or expired gas, i.e., carbon dioxide, in the patient's pharynx so as to provide an early indication of an interruption of proper respiration or breathing.

2. Discussion of the Prior Art

During surgical procedures in which a patient is placed under general anesthesia, an anesthetist or anesthesiologist continuously administers a general anesthetic (e.g. sodium pentothal/muscle relaxant) and manages the patient's respiration or breathing. Often, an endotracheal tube is fitted into the patient's trachea for administering anesthesia and other drugs, and a mechanical ventilator is used to pump oxygen into the patient's lungs and to extract therefrom expired carbon dioxide. To ensure that proper ventilation is taking place, it is common for the anesthetist to monitor the respective levels of (i) oxygen saturation in the patient's blood and (ii) the expired carbon dioxide. Pulse oximetry is the technique most often used to detect the level of blood oxygenation, and capnography is commonly used to monitor the expired carbon dioxide level. Of the two types of monitors for detecting proper ventilation, the carbon dioxide monitor is far quicker to indicate an interruption of ventilation since oxygen saturation can remain at a normal or near normal level for several minutes after proper ventilation has ceased. On the other hand, an interruption in ventilation will almost immediately give rise to a precipitous drop in the carbon dioxide level.

An increasingly popular alternative to general anesthesia is Monitored Anesthesia Care (MAC) with sedation. It differs from general anesthesia in that (a) much shorter-acting anesthetics (e.g., propofol or midazalam) are used to place the patient in a deep state of anesthesia, and (b) the patient is not put on a ventilator, i.e., the patient breathes by himself, just as if sleeping. Though shorter acting, MAC drugs are nonetheless potent hypnotics and analgesics. With the ever-increasing number of out-patient surgeries, many types of surgical procedures that were formerly performed under general anesthesia are now performed using this newer technique. In administering these drugs, it will be appreciated that the anesthetist must be highly skilled in airway management and especially attentive to the patient's breathing since, as noted, the patient is required to breath on his own.

During MAC anesthesia procedures, oxygen is commonly delivered to the patient either through a facial mask or through a nasal cannula. Either of such delivery devices enables the patient to achieve maximum oxygenation. As in the case of general anesthesia, oxygen saturation is typically measured by pulse oximetry, using an infrared sensor which is usually attached to the patient's finger, ear or toe. When a mask is used for administering oxygen, the level of expired carbon dioxide can be easily monitored by placing a capnograph sample line inside the mask. When a nasal cannula is used for administering oxygen, one of the two nasal prongs can be connected to the capnograph sample line while the other prong supplies oxygen. While both of these devices (i.e. the facial mask and nasal cannula) can be highly effective in delivering oxygen and monitoring expired gas, both can be problematic under certain circumstances. For example, a facial mask can interfere with most surgical procedures involving the patient's face and, hence, is usually not used during such procedures. On the other hand, a split nasal cannula can only be used when both nasal passages are clear and the patient is not breathing through the mouth. When either nasal passage is closed or even partially obstructed, either oxygen delivery or carbon dioxide monitoring is compromised. Thus, it is apparent that a need exists for a device that is capable of delivering oxygen and/or monitoring the level of expired gas without presenting the problems identified.

During MAC with sedation procedures, a patient may become so sedate that breathing will become slow or even stop all together. When a respiration failure is detected (as may also occur during an obstruction or closure of the patient's airway, e.g. by the patient's tongue falling back in the pharynx), the anesthetist must be quick to respond. Usually, proper breathing can be restored by a simple jaw thrust or a repositioning of the patient's head. But sometimes a mechanical "airway" must be inserted into the patient's pharynx, either through the mouth or nose, to clear the obstruction and restore proper breathing. A typical mechanical airway comprises a soft rubber tube having a length sufficient to pass any obstruction in the pharynx and to allow normal respiratory gas exchange through the tube. Usually, such airways have an arcuate shape to conform to the shape of the alimentary canal. While being adapted to maintain an open, unobstructed air passage, conventional airways are not adapted to deliver oxygen or the like, or to monitor the level of exhalant gas. In fact, when a facial mask is used to administer oxygen and to sense the carbon dioxide level, the anesthetist must be quick to reapply such mask after removing it to insert a mechanical airway so as to assure continuous blood oxygenation and carbon dioxide monitoring.

SUMMARY OF THE INVENTION

In view of the foregoing discussion, an object of this invention is to provide an improved pharyngeal airway device which, in addition to being adapted to maintain an open airway passage, is also adapted to deliver oxygen or other inhalant gas directly to a patient's pharynx, and to monitor the level of exhalant (expired) gas in the vicinity of a patient's trachea where the carbon dioxide level is greatest.

Another object of this invention is to provide an improved mechanical airway which obviates the need for either facial masks or split nasal cannulas for delivering inhalant and monitoring the level of expired gases.

Another object of this invention is to provide a device which is adapted for use with a conventional airway for delivering an inhalant gas at a proximal end of the airway, and/or for sampling the level of expired gas at the airway's distal end.

Another object of this invention is to provide an improved method for monitoring the level of expired gas from an anesthetized patient.

According to a preferred embodiment, the airway apparatus of the invention generally comprises a single channel, tubular member, preferably having an arcuate shape, which is adapted for insertion into a patient's pharynx, either through the mouth or nasal passage, to provide a mechanical airway which prevents obstruction during the administration of anesthesia. In contrast with conventional mechanical airways, the airway of the invention is provided with means for coupling a pair of gas lines to the interior channel of the airway through which oxygen or the like can be directly administered to the patient through the airway, and the level of exhalant gas ($CO_2$) can be sampled, again through the airway. Preferably, the inhalant gas line is connected to the proximal end of the airway, and the exhalant gas line is connected to the distal end of the airway. By virtue of its construction, the airway of the invention operates to maintain an open airway while simultaneously delivering optimum oxygenation, and providing for optimum detection of expired gas, so as to assure early detecting of a ventilation problem.

According to another embodiment of the invention, the tubular member which maintains an open airway has two side-by-side conduits or lumens which are spaced apart by a common septum or wall. Coupling means are provided for coupling an inhalant gas line to one conduit, and an exhalant gas sampling line to the other conduit.

According to another embodiment of the invention, a device is provided for use with a conventional airway for delivering oxygen or the like to the airway's proximal end, and/or for sampling expired gas at the airway's distal end. Such device comprises a pair of conduits or tubes which are adapted to slide into the internal passage of an airway to provide an inhalant gas at the proximal end, and/or to sample expired gas at the distal end when the airway is being used. Preferably, both of such conduits have a substantially L-shaped configuration, with one leg of one conduit being substantially equal in length to the corresponding leg of the other conduit, and with the other legs of the respective conduits being of unequal length, whereby the longer leg can extend to the distal end of the airway passage, while the shorter leg remains in the proximal end. Preferably the end of one conduit, opposite the shorter leg, is provided with a connector adapted to be connected to a source of an inhalant gas, and the end of the other conduit is provided with a different connector adapted to be connected to a capnograph line.

In accordance with another aspect of the invention, an improved method for monitoring the level of expired gas during anesthesia is characterized by the step of sensing the expired gas level within the posterior pharynx region where the expired gas concentration is relatively high and the detection thereof is not significantly effected by the flow of inhalant gas.

The invention will be better understood from the ensuing detailed description of preferred embodiments, reference being made to the accompanying drawings in which like reference characters denote like parts.

BRIEF DESCRIPTION OF THE DRAWINGS

FIGS. 4 through 7 are perspective illustrations of alternative embodiments of the invention.

DETAILED DESCRIPTION OF PREFERRED EMBODIMENTS

Figure 1A:
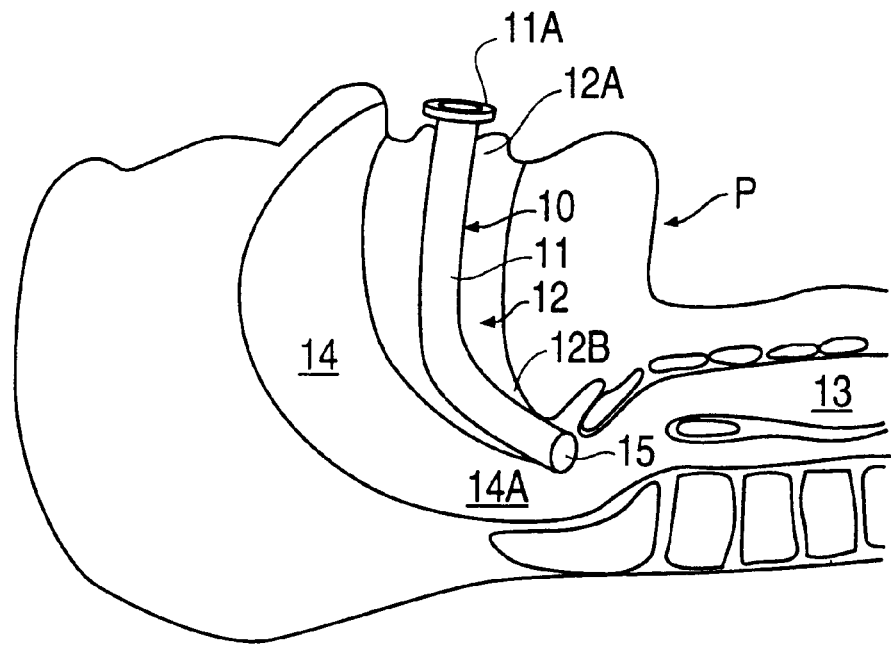
FIGS. 1A and 1B (Prior Art) illustrate conventional oropharyngeal and nasopharyngeal airways positioned in the pharynx of a patient undergoing anesthesia.
Figure 1B:
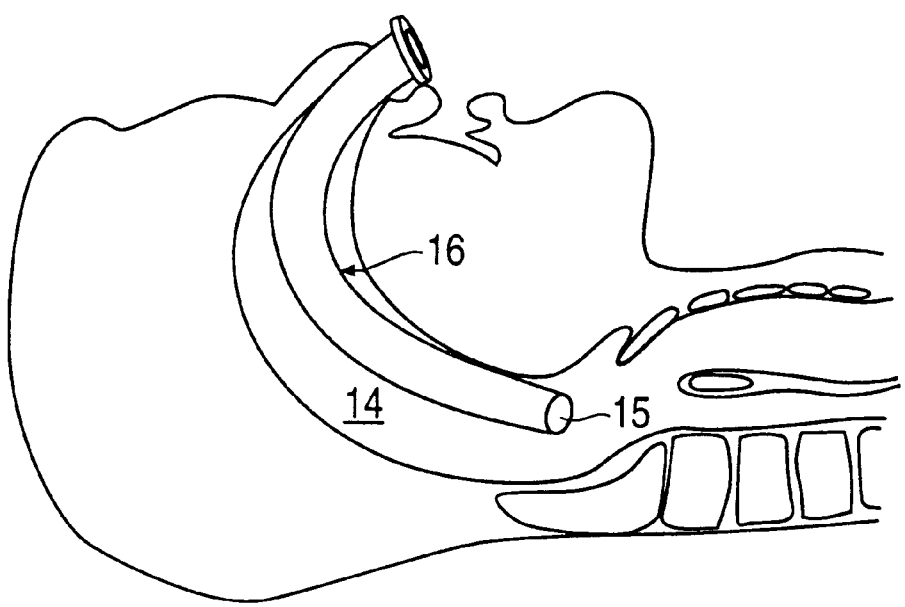

Referring now to the drawings and particularly to FIG. 1A, a conventional oropharyngeal airway 10 is shown positioned in the oral cavity 12 of a patient P. Airway 10 commonly comprises a relatively pliable tube made 11, for example, of latex, silicone rubber or a soft polyvinylidene chloride (PVC) and having an outside diameter of about 25 mm, and an inside diameter of about 20 mm. The length of tube 11 is typically about 15– 20 cm. so as to extend from the anterior pharynx region 12A, beginning at the entrance of the mouth, to the posterior pharynx region 12B, in the vicinity of the base of the tongue where the tongue joins with the posterior region of the nasopharyngeal cavity 14. Tube 11 is usually provided with a flared end 11A which abuts the patient's lips when the airway is fully inserted. The airway is often given an arcuate shape to conform somewhat to the pharyngeal passageway and in order to facilitate insertion. The wall of the airway is sufficiently rigid to prevent the patient's tongue from collapsing the tube wall and thereby obstructing the patient's alimentary canal (i.e., the patient's airway). In use, the airway also enables normal respiratory gas exchange through the conduit 15 defined by the tube structure. A conventional nasopharyngeal airway 16 is shown in use in FIG 1B. Airway 16 is virtually identical to airway 10, except that its diameter is somewhat smaller to facilitate insertion through the nasal passage.

Figure 2:
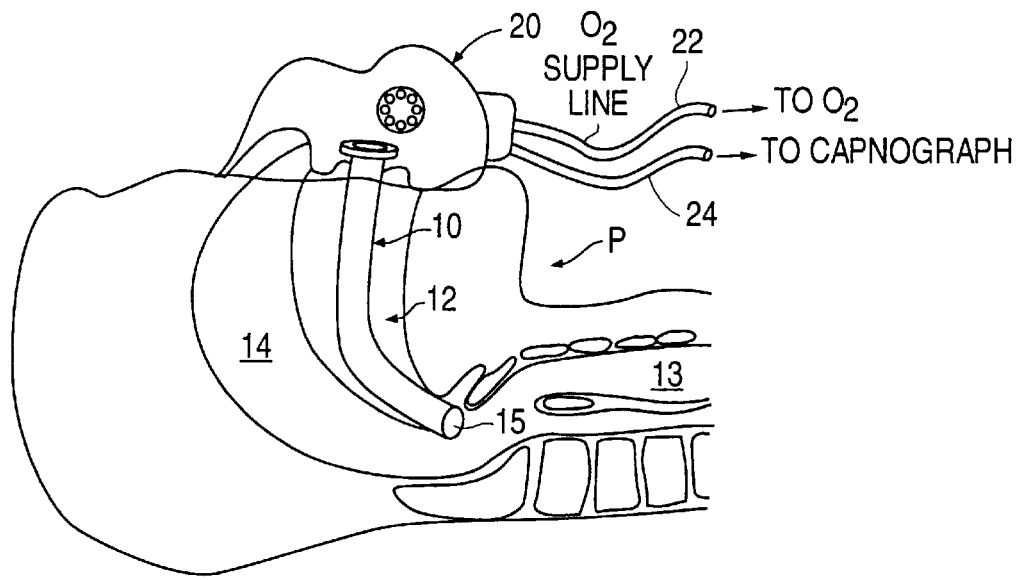
FIG. 2 (Prior Art) illustrates the combined use of a conventional oropharyngeal airway and face mask for delivering an inhalant gas and for monitoring expired gas.

As noted above, a mechanical airway of the type described above is often used only after a patient has obstructed during the administration of anesthesia and/or other drugs and proper breathing has been interrupted. In FIG. 2, an oropharyngeal airway 10 is shown in use while a facial mask 20 has been applied to both (a) administer an inhalant gas, typically oxygen, which is provided to the mask through an inhalant gas line 22, and (b) monitor the level of carbon dioxide gas expired by the patient. An expired gas sampling line 24 is connected between the mask and a capnograph to detect the level of carbon dioxide within the mask. As may be appreciated, the need for both a sterile airway and mask increases the expense of the surgical procedure.

Figure 3:
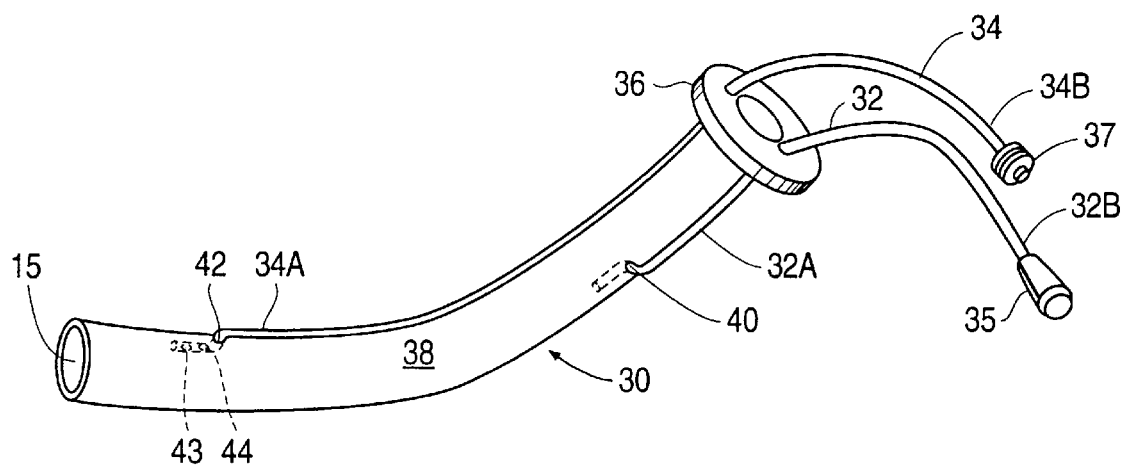
FIG. 3 is a perspective illustration of a pharyngeal airway structured in accordance with a preferred embodiment of the invention.

Now in accordance with the present invention, the need for the combination of (i) a mechanical airway to maintain an open air passage, and (ii) a facial mask (or a split nasal cannula) to both deliver oxygen or the like to a sedated patient, and to monitor the level of gas expired by such patient is totally obviated by the new and improved airway 30 illustrated in FIG. 3. Preferably, airway 30 is similar in size, shape and construction to a conventional nasopharyngeal 16 described above, being a rubber-like tube about 15–20 cm. in length, having an outside diameter of about 12–15 mm, and having a wall thickness of about 1–2 mm. However, rather than operating to merely maintain an open air passage in the patient, the airway of the invention is adapted to deliver an inhalant gas, provided through an associated inhalant gas delivery line 32, as well as to sample the level of expired gas through an associated gas sampling line 34. Preferably, the inhalant gas sample line 32 is connected to the proximal end portion 30A of airway 32, and the expired gas sampling line 34 is connected to the distal portion 30B of the airway. By this arrangement, the inhalant gas does not swamp out the relatively low concentration of expired gas at the proximal end, and the expired gas is sampled at a location deep within the patient's pharynx, at the top of the trachea 13, where the expired gas concentration is significantly greater than at the anterior of the pharynx where the expired gas concentration is commonly monitored. Preferably, gas lines 32 and 34 pass through the flared portion 36 of the airway and run parallel to the tubular portion 38 of the airway, along the external surface thereof. One end 32A of the inhalant gas line enters a small hole 40 formed near the proximal end portion of the airway and terminates inside the tubular member in close proximity of the hole. The opposite end 32B of the inhalant gas line is fitted with a female coupling 35 which is adapted to be connected to another gas line which, in turn, is connected to an inhalant gas supply (not shown) which can supply inhalant gas, e.g., oxygen, at a rate of from 3–6 liters per minute. Similarly, one end 34A of the exhalant gas sampling line enters a small hole 42 formed in the distal portion of the airway and extends a short distance inside the tubular member. Preferably, the end portion 34A of the exhalant gas line is provided with two or three additional holes 43, 44, in the side wall thereof to assure exhalant gas can be sampled even if mucous or the like were to clog the end of the gas-sampling line. The opposite end 34B of the exhalant gas sampling line is fitted with a male coupling 37 which is adapted to be connected to a capnograph (not shown). Preferably, couplings 35 and 37 differ from each other to avoid any potential mistake in connecting the lines to the proper sources. Preferably, each of the gas lines 32,34 are made of polyethylene tube and have a diameter of about 2–5 mm.

Figure 4:
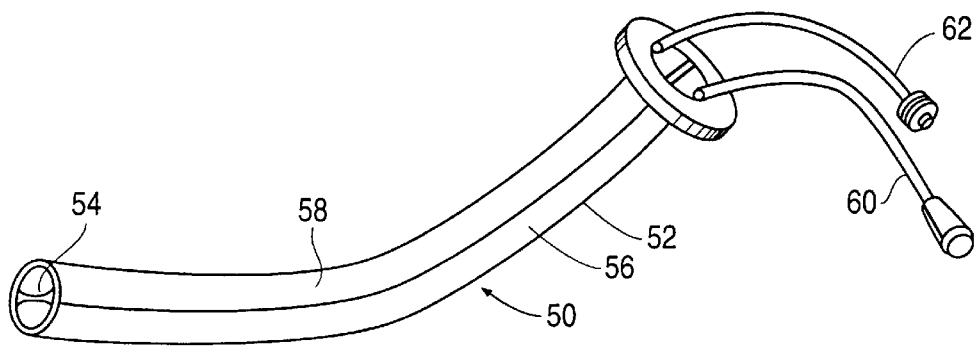
Figure 5:
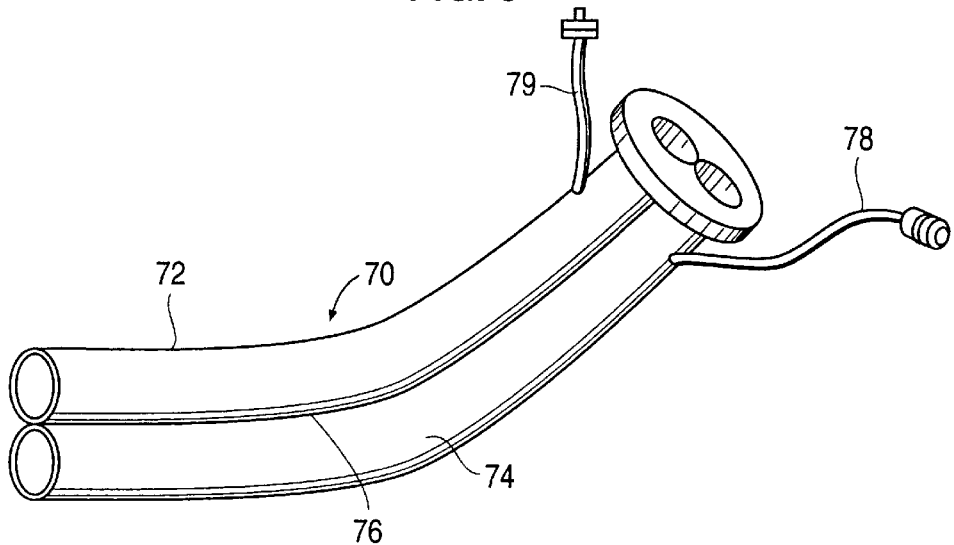
Figure 6:
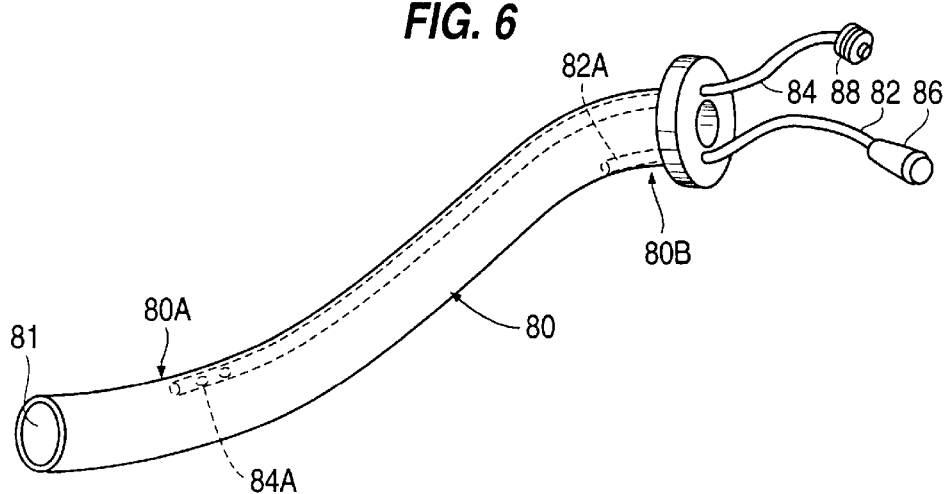

Alternative airways embodying the invention are shown in FIGS. 4 through 6. In FIG. 4, airway 50 is shown to comprise a tubular member 52 of circular cross-section. A septum 54 divides the internal conduit in half to define two side-by-side conduits 56,58 which share a common wall, i.e., the septum. Inhalant and exhalant gas lines 60,62 are connected to each of the conduits 56, 58 at the proximal end 50A of the airway. Because of the physical separation between the conduits, there is no need to guard against a washout of the exhalant gas signal by the incoming inhalant gas, and the exhalant gas sample line need not extend to the distal portion of the airway.

In FIG. 5, an airway 70 takes the form of two tubular lumens 72, 74 which are joined together along a common boundary or wall 76. Preferably, the dual lumen/conduit airways 50, 70 are produced by an injection molding process.

In FIG. 6, a highly preferred airway 80 defines a single internal lumen 81 containing a pair of gas lines 82, 84. Gas line 82 is adapted to be connected to an inhalant gas source through a female coupling 86. The opposite end 82A of gas line 82 is positioned within the proximal end of the airway's lumen and is held in place by a suitable adhesive, strap or other fastening means. Gas line 84 is adapted to be connected to a gas-sampling device through a male coupling 88. The opposite end 84A of gas line 84 is positioned within the distal end 80A of the airway, and is similarly affixed thereto by an adhesive, strap or other fastening means. It is also contemplated that those portions of gas lines 82, 84 located within the airway lumen can comprise tubes integrally formed in the inside wall of the airway, and the external portions of the two gas lines can be press fit into such tubes.

In FIG. 7, another embodiment of the invention, is shown to comprise a device 90 which is adapted for use with a conventional airway 92 (shown in phantom) for delivering oxygen or the like to the vicinity of the airway's proximal end 92A, and for sampling expired gas in the vicinity of the airway's distal end 92B. Such device comprises a pair of conduits 94,96 adapted to fit within the internal passage 92C of the airway. Each of such conduits has a substantially L-shaped configuration, each having a first leg 94A, 96A, and a second leg 94B, 96B arranged on opposites of a bent portion 94C, 96C. Legs 94A and 96A may be of equal length, as shown, and legs 94B and 96B are of unequal length, leg 96B being substantially longer than leg 94B. Thus, when the conduits are inserted into the airway passage, as shown, with the bent portion 94C resting on the rim 92D of the airway, the end of leg portion 96B extends to the vicinity of the distal end of the airway passage and is positioned to sample expired gas when the airway is in use, and the end of leg 94B extends a short distance into the proximal portion of the airway passage, in a position to administer an inhalant gas. Preferably, legs 94B and 96B are contiguously arranged and may be bonded together. Legs 94A and 96A are preferably separated to facilitate the connection of leg 94A to a source of inhalant gas, and to facilitate the connection of leg 96A to a capnogrph. Preferably, the connectors 100 and 102 at the ends of legs 94A and 96A are different to avoid any mistake in connecting the conduits to the proper line. The desired length of the unequal legs 94b and 96B is measured from the bend in each airway. In use, a clamp or piece of tape (not shown) may be used to affix the device to the airway, as shown. As in the case of the embodiments shown in FIGS. 3–6, each of the conduits (gas lines) 94,96 is preferably made of polyethylene and has a diameter of about 2–5 mm.

While the invention has been disclosed with reference to certain preferred embodiments, it will be appreciated that variations can be made without departing from the spirit of the invention, and such variations are intended to fall within the scope of the appended claims.

What is claimed is:

1. A device adapted for use with an oro/nasopharyngeal airway for delivering an inhalant gas to a proximal end of said airway and for sampling expired gas at a distal end of said airway, said device comprising first and second conduits which are adapted to slide into an internal passage of said airway to provide an inhalant gas in the vicinity of the proximal end of said airway and to sample expired gas in the vicinity of the distal end of said airway when the airway is being used, one conduit terminating within said internal passage in the vicinity of said proximal end, and the other conduit terminating within said internal passage in the vicinity of said distal end.

2. The device as defined by claim 1 wherein respective ends of said conduits are provided with gas line connectors of different types.

3. The device as defined by claim 1 wherein each of such conduits has a substantially L-shaped configuration defined by first and second leg portions separated by a bent portion, the respective first leg portions of each conduit being of unequal length so that in the event said first leg portions are inserted into said airway passage to the point that the bent portions rest upon an outer rim of said airway, an end of one of said first leg portions is located in the vicinity of the distal end of said airway passage at a position to sample and expired gas when said airway is in use, and an end of the other of said first leg portions is located in the vicinity of the proximal end portion of said airway at a position to administer an inhalant gas.

4. The device as defined by claim 3 wherein the ends of the respective second leg portions have gas line connectors of different types affixed thereto.

5. The device as defined by claim 3 wherein a conduit wall defining said first leg portion of said conduit which is to be located in the vicinity of the distal end of said airway is provided with a plurality of axially spaced holes.

6. The device as defined by claim 1 wherein a portion of said first and second conduits are contiguously arranged within said internal passage.

7. The device as defined by claim 6 wherein said contiguous portions are bonded together.

* * * * *